United States Patent
Cao et al.

(10) Patent No.: US 9,598,397 B2
(45) Date of Patent: Mar. 21, 2017

(54) PROCESS FOR MAKING REVERSE TRANSCRIPTASE INHIBITORS

(71) Applicant: Merck Sharp & Dohme Corp., Rahway, NJ (US)

(72) Inventors: Yang Cao, Scotch Plains, NJ (US); Donald R. Gauthier, Jr., Westfield, NJ (US); Guy R. Humphrey, Hillsborough, NJ (US); Tetsuji Itoh, Somerset, NJ (US); Michel Journet, Somerset, NJ (US); Gang Qian, So. Brunswick, NJ (US); Benjamin D. Sherry, New York, NY (US); David M. Tschaen, Holmdel, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/100,940

(22) PCT Filed: Dec. 2, 2014

(86) PCT No.: PCT/US2014/068008
§ 371 (c)(1),
(2) Date: Jun. 1, 2016

(87) PCT Pub. No.: WO2015/084763
PCT Pub. Date: Jun. 11, 2015

(65) Prior Publication Data
US 2016/0297794 A1    Oct. 13, 2016

Related U.S. Application Data

(60) Provisional application No. 62/017,542, filed on Jun. 26, 2014, provisional application No. 61/911,686, filed on Dec. 4, 2013.

(51) Int. Cl.
*C07D 401/06* (2006.01)
*C07D 213/69* (2006.01)
*C07D 213/78* (2006.01)

(52) U.S. Cl.
CPC ......... *C07D 401/06* (2013.01); *C07D 213/69* (2013.01); *C07D 213/78* (2013.01)

(58) Field of Classification Search
None
See application file for complete search history.

(56) References Cited

U.S. PATENT DOCUMENTS

| | | |
|---|---|---|
| 2007/0021442 A1 | 1/2007 | Saggar et al. |
| 2010/0034813 A1 | 2/2010 | Xia et al. |
| 2010/0256181 A1* | 10/2010 | Tucker ................ C07D 401/06 514/303 |
| 2011/0245296 A1 | 10/2011 | Burch et al. |
| 2013/0005744 A1 | 1/2013 | Wolkenberg et al. |

FOREIGN PATENT DOCUMENTS

| | | |
|---|---|---|
| WO | 2011120133 A1 | 10/2011 |
| WO | 2014052171 A1 | 4/2014 |
| WO | 2014089140 A1 | 6/2014 |

OTHER PUBLICATIONS

Cowden, et al, "A New Synthesis of 1,2,4-Triazolin-5-ones: Application to the Convergent Synthesis of an NK1 Antagonist", Tetrahedron Letters, 2000, pp. 8661-8664, vol. 41, No. 44, WO.
Jiang, B., et al, "Convenient Approaches to 4-Trifluoromethylpyridine", Organic Process Research & Developement, 2001, pp. 531-534, vol. 5.
Kondratov, I.S., et al, "New Synthetic Approach to Mevalonate and Mevaldate Fluoroanalogues", Tetrahedron: Asymmetry, 2007, pp. 1918-1925, vol. 18.

* cited by examiner

*Primary Examiner* — Timothy R Rozof
(74) *Attorney, Agent, or Firm* — Carol S. Quagliato; Catherine D. Fitch

(57) ABSTRACT

The present invention is directed to a novel process for synthesizing 3-(substituted phenoxy)-1-[(5-oxo-4,5-dihydro-1H-1,2,4-triazol-3-yl)methyl])-pyridin-2(1H)-one derivatives. The compounds synthesized by the processes of the invention are HIV reverse transcriptase inhibitors useful for inhibiting reverse transcriptase and HIV replication, and the treatment of human immunodeficiency virus infection in humans.

23 Claims, 1 Drawing Sheet

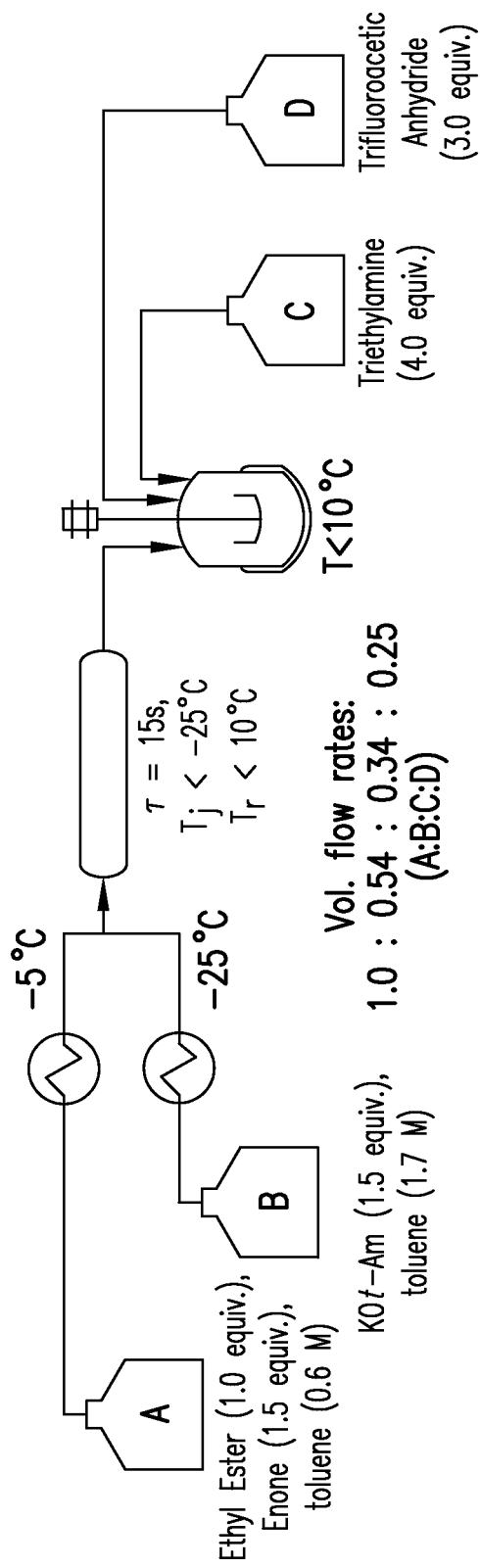

PROCESS FOR MAKING REVERSE TRANSCRIPTASE INHIBITORS

RELATED APPLICATIONS

This application is a 35 U.S.C. §371 filing from International Application No. PCT/US2014/068008, filed Dec. 2, 2014, which claims the benefit of U.S. Provisional Application No. 62/017,542, filed Jun. 26, 2014, and U.S. Provisional Application No. 61/911,686, filed Dec. 4, 2013. Each of the aforementioned applications is herein incorporated by reference in its entirety.

BACKGROUND OF THE INVENTION

The retrovirus designated human immunodeficiency virus (HIV), particularly the strains known as HIV type-1 (HIV-1) and type-2 (HIV-2), have been etiologically linked to the immunosuppressive disease known as acquired immunodeficiency syndrome (AIDS). HIV seropositive individuals are initially asymptomatic but typically develop AIDS related complex (ARC) followed by AIDS. Affected individuals exhibit severe immunosuppression which makes them highly susceptible to debilitating and ultimately fatal opportunistic infections. Replication of HIV by a host cell requires integration of the viral genome into the host cell's DNA. Since HIV is a retrovirus, the HIV replication cycle requires transcription of the viral RNA genome into DNA via an enzyme known as reverse transcriptase (RT).

Reverse transcriptase has three known enzymatic functions: The enzyme acts as an RNA-dependent DNA polymerase, as a ribonuclease, and as a DNA-dependent DNA polymerase. In its role as an RNA-dependent DNA polymerase, RT transcribes a single-stranded DNA copy of the viral RNA. As a ribonuclease, RT destroys the original viral RNA and frees the DNA just produced from the original RNA. And as a DNA-dependent DNA polymerase, RT makes a second, complementary DNA strand using the first DNA strand as a template. The two strands form double-stranded DNA, which is integrated into the host cell's genome by the integrase enzyme.

It is known that compounds that inhibit enzymatic functions of HIV RT will inhibit HIV replication in infected cells. These compounds are useful in the prophylaxis or treatment of HIV infection in humans. Among the compounds approved for use in treating HIV infection and AIDS are the RT inhibitors 3'-azido-3'-deoxythymidine (AZT), 2',3'-dideoxyinosine (ddI), 2',3'-dideoxycytidine (ddC), d4T, 3TC, nevirapine, delavirdine, efavirenz, abacavir, emtricitabine, and tenofovir.

The RT inhibitor 3-chloro-5-({1-[(4-methyl-5-oxo-4,5-dihydro-1H-1,2,4-triazol-3-yl)methyl]-2-oxo-4-(trifluoromethyl)-1,2-dihydropyridin-3-yl}oxy)benzonitrile, related compounds and methods for making the same are illustrated in WO 2011/120133 A1, published on Oct. 6, 2011, and US 2011/0245296 A1, published on Oct. 6, 2011, both of which are hereby incorporated by reference in their entirety. The present invention is directed to a novel process for synthesizing 3-(substituted phenoxy)-1-[(5-oxo-4,5-dihydro-1H-1,2,4-triazol-3-yl)methyl])-pyridin-2(1H)-one derivatives. The compounds synthesized by the processes of the invention are HIV reverse transcriptase inhibitors useful for inhibiting reverse transcriptase and HIV replication, and the treatment of human immunodeficiency virus infection in humans.

SUMMARY OF THE INVENTION

The present invention is directed to a novel process for synthesizing 3-(substituted phenoxy)-1-[(5-oxo-4,5-dihydro-1H-1,2,4-triazol-3-yl)methyl])-pyridin-2(1H)-one derivatives. The compounds synthesized by the processes of the invention are HIV reverse transcriptase inhibitors useful for inhibiting reverse transcriptase and HIV replication, and the treatment of human immunodeficiency virus infection in humans.

BRIEF DESCRIPTION OF THE DRAWINGS

FIG. 1 shows a schematic of the flow reactor for the aldol condensation step used in the process for synthesizing 3-(substituted phenoxy)-1-[(5-oxo-4,5-dihydro-1H-1,2,4-triazol-3-yl)methyl])-pyridin-2(1H)-one.

DETAILED DESCRIPTION OF THE INVENTION

The invention encompasses a method for synthesizing a compound of Formula I

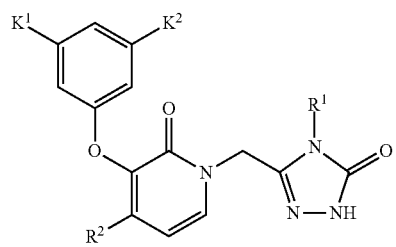

I wherein $R^1$ is $C_{1-6}$ alkyl, $K^1$ and $K^2$ are independently $CH_3$, $CF_3$, $CHF_2$, $CH_2CF_3$, $OCH_3$, Cl, Br, F, CN or $SCH_3$, and $R^2$ is $CF_3$, Cl or Br, comprising Step 1—conducting an aldol addition of an ester of Formula B

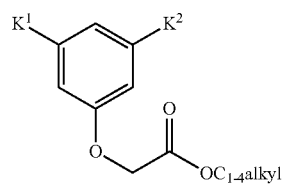

B with a compound of Formula C

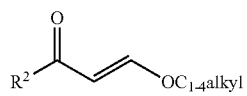

C in the presence of a first base in a hydrocarbon or ethereal organic solvent at a first reduced temperature, wherein the first base is a metal alkoxide or metal amide base, to form Intermediate D, and optionally isolating Intermediate D

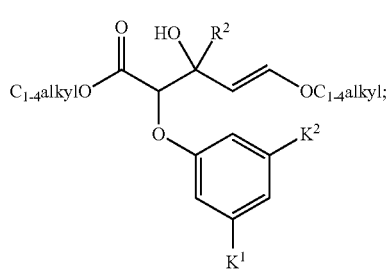

D

Step 2—reacting Intermediate D with an organic acid anhydride or sulfonyl chloride in the presence of a second base, wherein the second base is a tertiary amine base, at a second reduced temperature in a hydrocarbon or ethereal organic solvent, which solvent can be the same or different as that in Step 1, to form Intermediate E, and optionally isolating Intermediate E

E

Step 3—cyclizing Intermediate E in the presence of a nitrogen source having formula $NH_{3+n}X_n$, wherein $X_n$=a non-coordinating counteranion and n=0 (zero) or 1, at a first elevated temperature in a mixture of alcohol and organic solvent to make a compound of Formula F

F and
Step 4—coupling the compound of Formula F with a compound of Formula A

A wherein $X^1$ is a leaving group,
in the presence of a third base selected from an inorganic base or a tertiary amine base in a polar aprotic or protic solvent to yield the compound of Formula I.

Alternatively, after performing Steps 1 and 2 as described above, Steps 3 and 4 described above can be replaced with Step 3A as follows:

Step 3A—cyclizing Intermediate E in the presence of a compound of Formula A

A wherein $X^1$ is $NH_2$, at an elevated temperature in a mixture of alcohol and organic solvent to make a compound of Formula I.

The following scheme is an example of Step 3A.

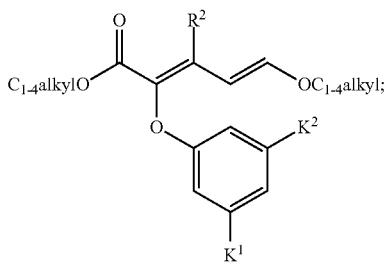

The invention also encompasses a method for synthesizing a compound of Formula F

F wherein $K^1$ and $K^2$ are independently $CH_3$, $CF_3$, $CHF_2$, $CH_2CF_3$, $OCH_3$, Cl, Br, F, CN or $SCH_3$, and $R^2$ is $CF_3$, Cl or Br,
comprising
Step 1—conducting an aldol addition of an ester of Formula B

B with a compound of Formula C

C in the presence of a first base in a hydrocarbon or ethereal organic solvent at a first reduced temperature, wherein the first base is a metal alkoxide or metal amide base, to form Intermediate D, and optionally isolating Intermediate D

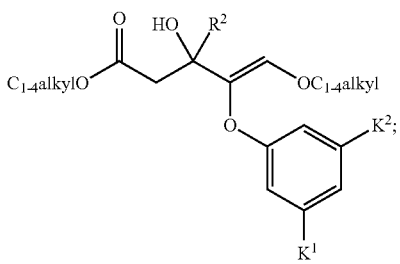

D

Step 2—reacting Intermediate D with an organic acid anhydride or sulfonyl chloride in the presence of a second base, wherein the second base is a tertiary amine base, at a second reduced temperature in a hydrocarbon or ethereal organic solvent, which solvent can be the same or different as that in Step 1, to form Intermediate E, and optionally isolating Intermediate E

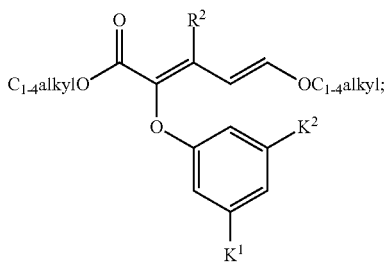

E

Step 3—cyclizing Intermediate E in the presence of a nitrogen source having formula $NH_{3+n}X_n$, wherein $X_n$=a non-coordinating counteranion and n=0 or 1, at a first elevated temperature in a mixture of alcohol and organic solvent to make the compound of Formula F.

The term "alkyl" means straight or branched alkyl chains of the indicated number of carbon atoms, including for example, methyl (Me), ethyl (Et), propyl (Pr, n-Pr) isopropyl (i-Pr, i-Pr or $^i$Pr) or tert-butyl (t-butyl, t-butyl).

The first base is a metal alkoxide or metal amide base, for example. In an embodiment of the invention, the first base is selected from: potassium tert-amylate, sodium bis(trimethylsilyl)amide, potassium or sodium tert-butoxide, lithium diisopropylamide or sodium or potassium ethoxide. In another embodiment of the invention, the first base is potassium ten-amylate or sodium bis(trimethylsilyl)amide.

The first reduced temperature and second reduced temperature are temperatures below room temperature. In an embodiment, the first reduced temperature is in a range of about 15° C. to about −50° C. In an embodiment, the second reduced temperature is in a range of about 15° C. to about −50° C. In another embodiment, the second reduced temperature is in a range of about 0° C. to about 10° C.

Hydrocarbon and ethereal organic solvents that may be utilized with the invention are known in the art and are, for example, tetrahydrofuran, diethyl ether, methyl tert-butyl ether, 2-methyltetrahydrofuran, toluene or xylenes. In an embodiment, the hydrocarbon or ethereal organic solvent is selected from: toluene or tetrahydrofuran. In another embodiment, the hydrocarbon or ethereal organic solvent is toluene.

The term "organic acid anhydride or sulfonyl chloride" includes, for example acetic anhydride, trifluoroacetic anhydride, methanesulfonyl chloride, trifluoromethanesulfonyl chloride, or p-toluenesulfonyl chloride. In an embodiment of the invention, the organic acid anhydride or sulfonyl chloride is selected from: trifluoroacetic anhydride, acetic anhydride or methanesulfonyl chloride. In another embodiment, the organic acid anhydride or sulfonyl chloride is selected from: trifluoroacetic anhydride or methanesulfonyl chloride.

The second base is a tertiary amine base. The third base is an inorganic or tertiary amine base. Inorganic bases include, for example, sodium hydroxide, lithium hydroxide, potassium hydroxide, sodium carbonate, lithium carbonate, potassium carbonate, cesium hydroxide, cesium carbonate, sodium hydrogen carbonate, potassium hydrogen carbonate, lithium hydrogen carbonate, lithium fluoride, sodium fluoride, potassium fluoride, cesium fluoride, lithium tert-butoxide, sodium tert-butoxide, potassium tert-butoxide, sodium phosphate and potassium phosphate. Tertiary amine bases include for example trimethylamine, dimethylethylamine, triethylamine, 1,4-diazobicyclo-[2,2,2]-octane, diisopropylethylamine, dicyclohexylethylamine. Suitable non-polar aprotic solvents include for example tetrahydrofuran, ethyl acetate, acetone, dimethylformamide, acetonitrile, dimethyl sulfoxide, dimethylacetomide, N-methylpyrrolidinone. The first base, second base and third base are selected independently from each other.

In an embodiment of the invention, the second base is selected from: trimethylamine, dimethylethylamine, triethylamine, 1,4-diazobicyclo-[2,2,2]-octane, diisopropylethylamine or dicyclohexylethylamine. In another embodiment of the invention, the second base is triethylamine.

In an embodiment, the third base is selected from: sodium hydroxide, lithium hydroxide, potassium hydroxide, sodium carbonate, lithium carbonate, potassium carbonate, cesium hydroxide, cesium carbonate, sodium hydrogen carbonate, potassium hydrogen carbonate, lithium hydrogen carbonate, lithium fluoride, sodium fluoride, potassium fluoride, cesium fluoride, lithium tert-butoxide, sodium tert-butoxide, potassium tert-butoxide, sodium phosphate, potassium phosphate, trimethylamine, dimethylethylamine, triethylamine, 1,4-diazobicyclo-[2,2,2]-octane, diisopropylethylamine, or dicyclohexylethylamine. In another embodiment, the third base is N,N-diisopropylethylamine.

Another embodiment of the invention encompasses a method for synthesizing the compound of Formula I or Formula F in accordance with the invention, wherein Intermediate D and Intermediate E are not isolated and Step 1 and Step 2 are conducted in a flow reactor comprising two feed solution inlets and an outlet to a receiving vessel, wherein:

the ester of Formula B and the compound of Formula C in the hydrocarbon or ethereal organic solvent were pumped to one flow reactor inlet;

the first base in the hydrocarbon or ethereal organic solvent was pumped to the second flow reactor inlet;

the organic acid anhydride or sulfonyl chloride was added continuously to the receiver vessel;

and the second base was added continuously to the receiver vessel. A flow reactor that can be utilized in accordance with the invention is illustrated in FIG. 1

For purpose of this specification, the term nitrogen source means a compound of the generic formula $NH_{3+n}X_n$, wherein $X_n$=a non-coordinating counteranion and n=0 or 1. A non-coordinating counteranion is for example, tetrafluoroborate, hexafluorophosphate, hexafluoroantimonate or trifluoromethanesulfonate. In an embodiment of the invention the $NH_{3+n}X_n$ nitrogen source is ammonium tetrafluoroborate, wherein n=1 and X=tetrafluoroborate. In another embodiment of the invention the $NH_{3+n}X_n$ nitrogen source is ammonia, wherein n=0. In another embodiment, the nitrogen source is a compound of Formula A wherein $X^1$ is $NH_2$.

The term first elevated temperature means a temperature above room temperature. In an embodiment, the first elevated temperature is in a range of about 25° C. to about 80° C. In another embodiment, the first elevated temperature is in a range of about 60° C. to about 80° C.

A mixture of alcohol and organic solvent means a mixture of the two components in any ratio. The alcohol includes for example methanol, ethanol, n-propanol, isopropanol, ten-butanol, tert-amyl alcohol and the organic solvent includes for example: tetrahydrofuran, diethyl ether methyl tert-butyl ether, 2-methyltetrahydrofuran, toluene or xylenes.

The term "leaving group" means an atom or atom group that leaves from a substrate in a substitution or elimination reaction and includes for example halogen and sulfonate. In an embodiment, the invention encompasses the process described herein wherein $X^1$ is selected from: halogen, OMs (mesylate), OTs (tosylate), OBs (besylate), $OP(O)(OR^i)_2$, $OC(O)R^i$, $OC(O)OR^i$ or $OC(O)NR^iR^{ii}$, wherein $R^i$ and $R^{ii}$ are independently selected from H and $C_{1-6}$alkyl. In another embodiment, the invention encompasses the process described herein wherein $X^1$ is chloro.

The term polar aprotic or protic solvent means a solvent with a large dipole moment. The term polar aprotic or protic solvent includes dimethyl sulfoxide, N,N-dimethylformamide, N,N-dimethylacetamide, N-methylpyrrolidinone, sulfolane, methanol, ethanol, isopropanol, tert-amyl alcohol or water. In an example, the polar aprotic or protic solvent is a mixture of alcohol and organic amide. In another embodiment, the polar aprotic or protic solvent is a mixture of tert-amyl alcohol and N-methylpyrrolidinone.

Another embodiment of the invention encompasses the method for synthesizing a compound of Formula I as described above, wherein Step 4 is conducted at a second elevated temperature. The term second elevated temperature means a temperature above room temperature, and is independent from the first elevated temperature. In an embodiment, the second elevated temperature is in a range of about 25° C. to about 80° C. In another embodiment, the second elevated temperature is about 25° C.

The invention also encompasses a method for synthesizing the compound of Formula I as previously described wherein:
the first base is selected from: potassium tert-amylate or sodium bis(trimethylsilyl)amide;
the first reduced temperature is in a range of about 0° C. to about −50° C.;
the hydrocarbon or ethereal organic solvent is toluene;
the organic acid anhydride or sulfonyl chloride is selected from: trifluoroacetic anhydride or methanesulfonyl chloride;
the second base is triethylamine;
the second reduced temperature is in a range of about 0° C. to about 10° C.;
the nitrogen source is $NH_3$;
the first elevated temperature is in a range of about 60° C. to about 80° C.;
the mixture of alcohol and organic solvent is a mixture of methanol and toluene;
$X^1$ is chloro;
the third base is N,N-diisopropylethylamine; and
the first polar aprotic or protic solvent is a mixture of tert-amyl alcohol and N-methylpyrrolidinone.

The invention also encompasses a method for synthesizing the compound of Formula I or Formula F as previously described, further comprising making the ester of Formula

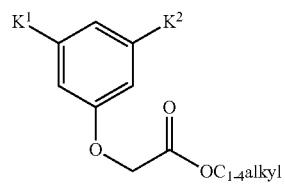

by reacting a compound of Formula G

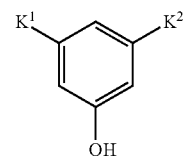

with a compound of Formula H

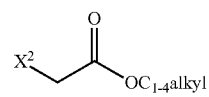

wherein $X^2$ is a halide or pseudo halide, in the presence of a fourth base in an organic polar aprotic solvent at a third elevated temperature, wherein the fourth base is a tertiary amine or inorganic carbonate, to make the ester of Formula B. In an embodiment of the invention, $X^2$ is bromo; the fourth base is N,N-diisopropylethylamine; the organic polar aprotic solvent N,N-dimethylformamide or acetone; and the third elevated temperature is about 50° C.

The term "pseudo halide" means for example methanesulfonate, p-toluenesulfonate, trifluoromethanesulfonate and diethyl phosphate.

The invention also encompasses any of the above-described methods for synthesizing the compound of Formula I wherein in the compound of Formula I $K^1$ is Cl, $K^2$ is CN, $R^1$ is $CH_3$ and $R^2$ is $CF_3$.

The invention also encompasses any of the above-described methods for synthesizing the compound of Formula F wherein in the compound of Formula I $K^1$ is Cl, $K^2$ is CN and $R^2$ is $CF_3$.

The compound 3-chloro-5-({1-[(4-methyl-5-oxo-4,5-dihydro-1H-1,2,4-triazol-3-yl)methyl]-2-oxo-4-(trifluoromethyl)-1,2-dihydropyridin-3-yl}oxy)benzonitrile has the following chemical structure.

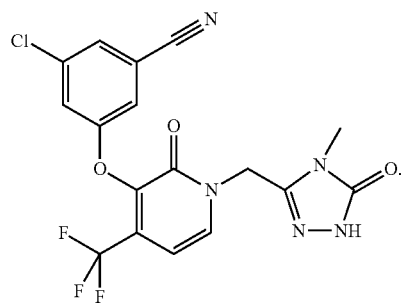 [SMILES: Cn1c(Cn2ccc(C(F)(F)F)c(Oc3cc(Cl)cc(C#N)c3)c2=O)n[nH]c1=O]

Anhydrous 3-chloro-5-({1-[(4-methyl-5-oxo-4,5-dihydro-1H-1,2,4-triazol-3-yl)methyl]-2-oxo-4-(trifluoromethyl)-1,2-dihydropyridin-3-yl}oxy)benzonitrile is known to exist in two crystalline forms, Form I and Form II. The differential scanning calorimetry (DSC) curve for crystalline anhydrous Form II shows an endotherm with an onset at 230.8° C., a peak maximum at 245.2° C., and an enthalpy change of 3.7 J/g, which is due to polymorphic conversion of anhydrous Form II to anhydrous Form I, and a second melting endotherm with an onset at 283.1° C., a peak maximum at 284.8° C., and an enthalpy change of 135.9 J/g, due to melting of anhydrous Form I. Production and the ability of this compound to inhibit HIV reverse transcriptase is illustrated in WO 2011/120133 A1, published on Oct. 6, 2011, and US 2011/0245296 A1, published on Oct. 6, 2011, both of which are hereby incorporated by reference in their entirety. This compound is useful for the treatment of human immunodeficiency virus infection in humans. Anhydrous crystalline Form I and Form II, and procedures for making Form II, are described in WO2014/052171, published on Apr. 3, 2014, which is hereby incorporated by reference in its entirety. Procedures for making anhydrous Form I are described in WO 2011/120133 and US 2011/0245296.

Previous known synthetic routes for synthesizing 3-chloro-5-({1-[(4-methyl-5-oxo-4,5-dihydro-1H-1,2,4-triazol-3-yl)methyl]-2-oxo-4-(trifluoromethyl)-1,2-dihydropyridin-3-yl}oxy)benzonitrile required more expensive raw materials, generated more waste and were more laborious to execute. The present invention is a simple, cost effective and reliable synthetic route for making the aforementioned compound.

The following examples illustrate the invention. Unless specifically indicated otherwise, all reactants were either commercially available or can be made following procedures known in the art. The following abbreviations are used:

ABBREVIATIONS

° C.=degrees Celsius
DMF=dimethylformamide
NMP=N-methylpyrrolidinone
g=gram(s)
IPA=isopropyl alcohol
NPA=n-propyl alcohol
L=liter(s)
mL=milliliter(s)
LC=liquid chromatography
LCAP=Liquid chromatography area percent
Me=methyl
h=hour(s)
Hz=Hertz
t=triplet
d=doublet
s=singlet
br s=broad singlet
IPA=2-propanol also known as n-propanol
NMR=Nuclear Magnetic Resonance
wt %=weight percent
nm=nanometer(s)
ug=microgram(s)
DMF=N,N-dimethylformamide
ppm=parts per million
Ph=phenyl
L=liter(s)
HPLC=High Pressure Liquid Chromatography
conc.=concentrated
KO$^t$Am=Potassium tert-amylate
$^t$AmOH=tert-amylalcohol
TFAA=trifluoroacetic anhydride
TEA=triethylamine
mp=melting point
GC/MS=gas chromatogtraphy/mass spectrometry
BHT=butylated hydroxytoluene
MTBE=tert-butylmethylether
wt=weight Example 1

Step 1

Phenyl Methylcarbamate

40% Aqueous methylamine (500 g, 6.44 mol) was charged to a 2 L vessel equipped with heat/cool jacket, overhead stirrer, temperature probe and nitrogen inlet. The solution was cooled to −5° C. Phenyl chloroformate (500.0 g, 3.16 mol) was added over 2.5 h maintaining the reaction temperature between −5 and 0° C. On complete addition the white slurry was stirred for 1 h at ~0° C.

The slurry was filtered, washed with water (500 mL) and dried under a nitrogen sweep overnight to afford 465 g (96% yield) of the desired product as a white crystalline solid; $^1$H NMR (CDCl$_3$, 500 MHz): δ 7.35 (t, J=8.0 Hz, 2H), 7.19 (t, J=8.0 Hz, 1H), 7.12 (d, J=8.0 Hz, 2H), 4.95 (br s, 1H), 2.90 (d, J=5 Hz, 3H).

Step 2

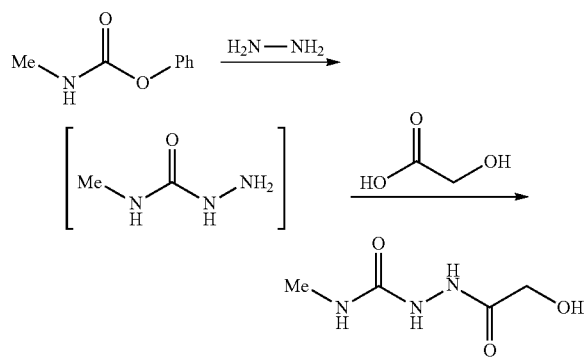

2-(2-Hydroxyacetyl)-N-methylhydrazinecarboxamide

Part A: Phenyl methylcarbamate (300 g, 1.95 mol) was charged to a 2 L vessel with cooling jacket, overhead stirrer, temperature probe, reflux condenser and nitrogen inlet. IPA (390 mL) was added at 23° C. Hydrazine hydrate (119 g, 2.33 mol) was added and the slurry heated to 75° C. for 6 h.

Part B: On complete reaction (>99% conversion by HPLC), IPA (810 mL) and glycolic acid (222 g, 2.92 mol) were added and the mixture stirred at 83-85° C. for 10-12 h. The reaction mixture was initially a clear colorless solution. The mixture was seeded with product (0.5 g) after 4 h at 83-85° C. The slurry was slowly cooled to 20° C. over 2 h and aged for 1 h. Seed was used to advance the crystallization, but the crystalline product can be precipitated and isolated without seed by allowing the solution to age at 83-85° C. for 4 hours.

The slurry was filtered and washed with IPA (600 mL). The cake was dried under a nitrogen sweep to afford 241.8 g (81% yield) of the desired product as a white crystalline solid: $^1$H NMR (D$_2$O, 500 MHz): δ 4.11 (s, 2H), 2.60 (s, 3H).

Step 3

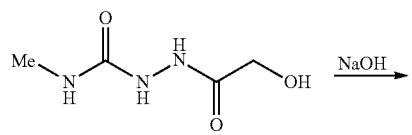

3-(Hydroxymethyl)-4-methyl-1H-1,2,4-triazol-5(4H)-one 2-(2-Hydroxyacetyl)-N-methylhydrazinecarboxamide (130 g @ ~95 wt %, 0.84 mol), n-propanol (130 mL) and water (130 mL) were charged to a 1 L vessel with jacket, overhead stirrer, temperature probe, reflux condenser and nitrogen inlet. Sodium hydroxide (pellets, 16.8 g, 0.42 mol) was added and the slurry warmed to reflux for 3 h. The reaction mixture was cooled to 20° C. and the pH adjusted to 6.5 (+/−0.5) using concentrated hydrochloric acid (28.3 mL, 0.34 mol). Water was azeotropically removed under vacuum at 40-50° C. by reducing the volume to ~400 mL and maintaining that volume by the slow addition of n-propanol (780 mL). The final water content was <3000 ug/mL. The resultant slurry (~400 mL) was cooled to 23° C. and heptane (390 ml) was added. The slurry was aged 1 h at 23° C., cooled to 0° C. and aged 2 h. The slurry was filtered, the cake washed with 1:2 n-PrOH/heptane (100 mL) and the filter cake was dried under a nitrogen sweep to provide 125 g (85% yield) of an off-white crystalline solid. The solid was ~73 wt % due to residual inorganics (NaCl): $^1$H NMR (CD$_3$OD, 500 MHz): δ 3.30 (s, 3H), 4.46 (s, 2H).

Step 4

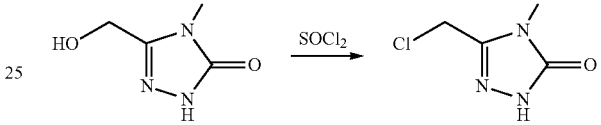

3-(Chloromethyl)-4-methyl-1H-1,2,4-triazol-5(4H)-one (1)

A mixture of 3-(Hydroxymethyl)-4-methyl-1H-1,2,4-triazol-5(4H)-one (54 g, at 73 wt %, 307 mmol) in ethyl acetate (540 mL) was stirred at 45° C. SOCl$_2$ (26.9 mL, 369 mmol) was added over 30-45 min and aged at 50° C. for 2 h. The reaction progress was monitored by HPLC. On complete reaction (>99.5% by area at 210 nm), the warm suspension was filtered and the filter cake (mainly NaCl) was washed with ethyl acetate (108 mL). The combined filtrate and wash were concentrated at 50-60° C. under reduced pressure to approximately 150 mL. The resulting slurry was cooled to −10° C. and aged 1 h. The slurry was filtered and the filter cake washed with ethyl acetate (50 mL). The cake was dried under a nitrogen sweep to afford 40.1 g (86% yield) of the desired product as a bright yellow solid: $^1$H NMR (CD$_3$OD, 500 MHz): δ 3.30 (s, 3H), 4.58 (s, 2H).

Example 2

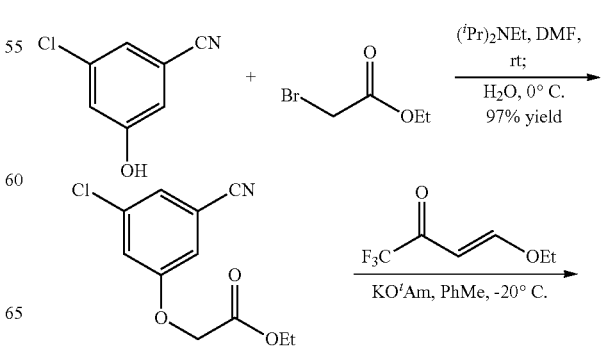

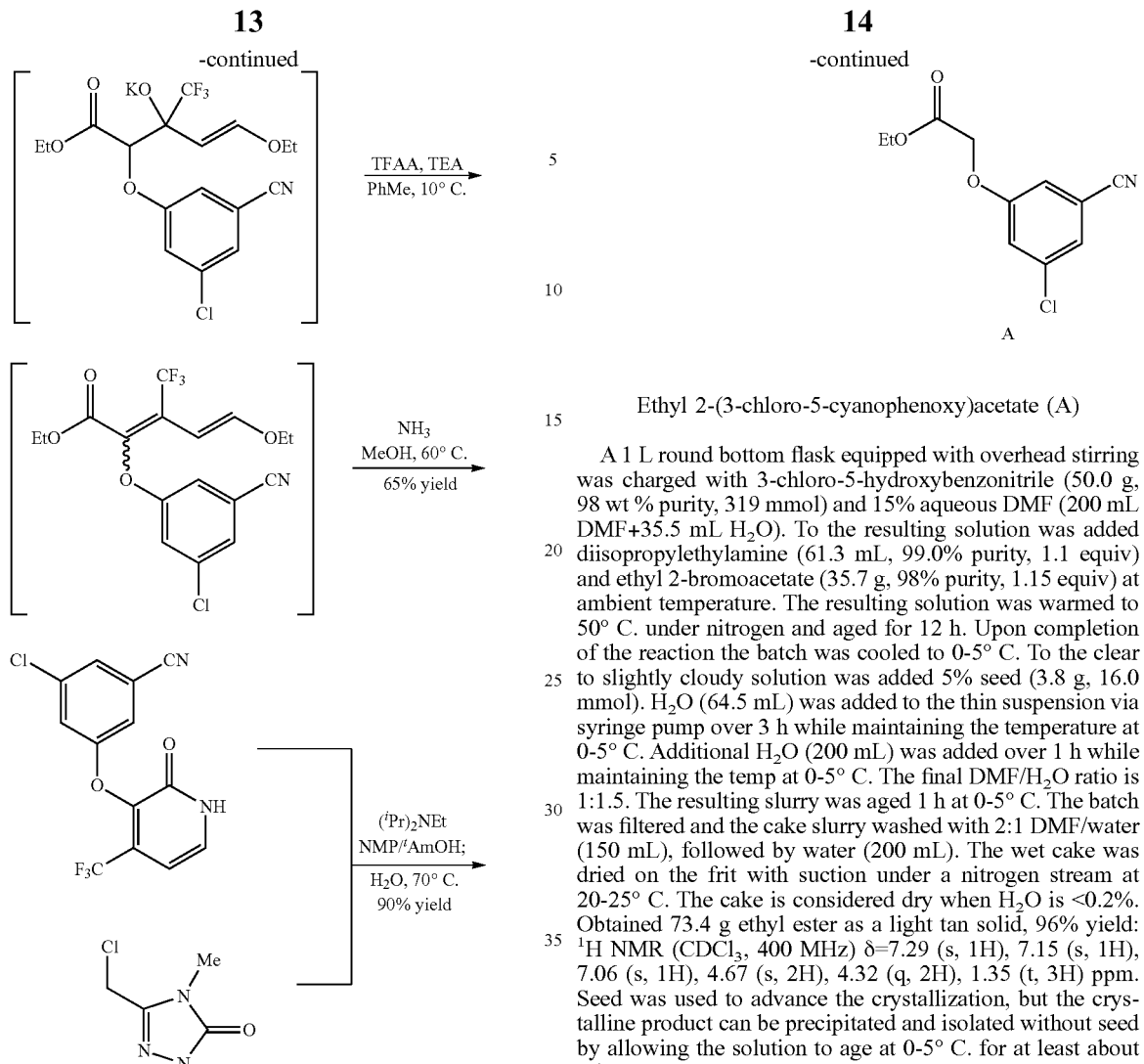

Ethyl 2-(3-chloro-5-cyanophenoxy)acetate (A)

A 1 L round bottom flask equipped with overhead stirring was charged with 3-chloro-5-hydroxybenzonitrile (50.0 g, 98 wt % purity, 319 mmol) and 15% aqueous DMF (200 mL DMF+35.5 mL H₂O). To the resulting solution was added diisopropylethylamine (61.3 mL, 99.0% purity, 1.1 equiv) and ethyl 2-bromoacetate (35.7 g, 98% purity, 1.15 equiv) at ambient temperature. The resulting solution was warmed to 50° C. under nitrogen and aged for 12 h. Upon completion of the reaction the batch was cooled to 0-5° C. To the clear to slightly cloudy solution was added 5% seed (3.8 g, 16.0 mmol). H₂O (64.5 mL) was added to the thin suspension via syringe pump over 3 h while maintaining the temperature at 0-5° C. Additional H₂O (200 mL) was added over 1 h while maintaining the temp at 0-5° C. The final DMF/H₂O ratio is 1:1.5. The resulting slurry was aged 1 h at 0-5° C. The batch was filtered and the cake slurry washed with 2:1 DMF/water (150 mL), followed by water (200 mL). The wet cake was dried on the frit with suction under a nitrogen stream at 20-25° C. The cake is considered dry when H₂O is <0.2%. Obtained 73.4 g ethyl ester as a light tan solid, 96% yield: $^1$H NMR (CDCl₃, 400 MHz) δ=7.29 (s, 1H), 7.15 (s, 1H), 7.06 (s, 1H), 4.67 (s, 2H), 4.32 (q, 2H), 1.35 (t, 3H) ppm. Seed was used to advance the crystallization, but the crystalline product can be precipitated and isolated without seed by allowing the solution to age at 0-5° C. for at least about 2 hours.

Step 2—Pyridone Synthesis

Synthetic Scheme

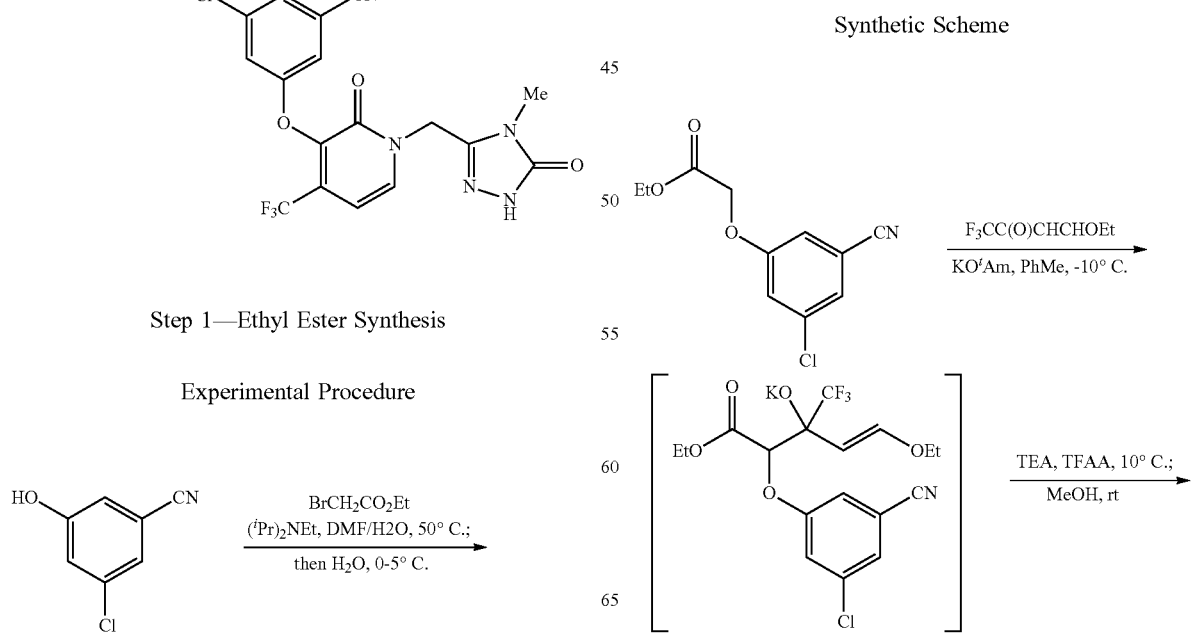

Step 1—Ethyl Ester Synthesis

Experimental Procedure

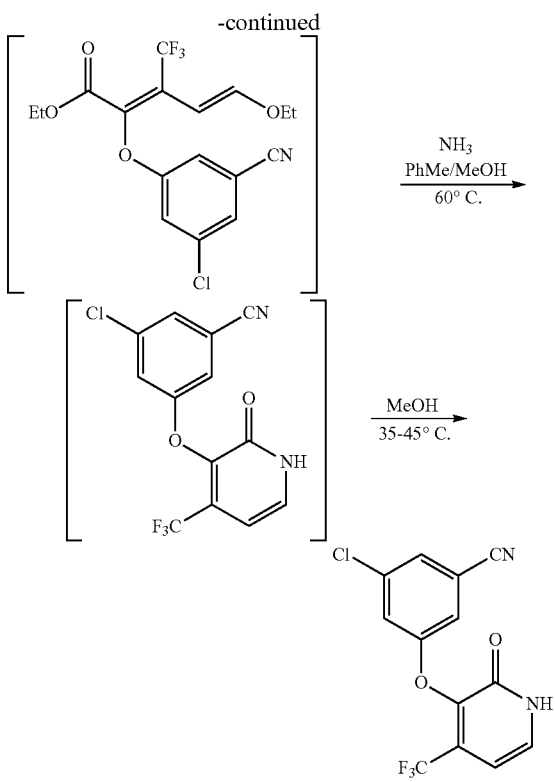

Experimental Procedures

Aldol Condensation (2E/Z,4E)-Ethyl 2-(3-chloro-5-cyanophenoxy)-5-ethoxy-3-(trifluoromethyl)penta-2,4-dienoate (C)

Ethyl 2-(3-chloro-5-cyanophenoxy)acetate (25.01 g, 104.4 mmol, 1.00 equiv) was charged to toluene (113.43 g, 131 mL) and 4-ethoxy-1,1,1-trifluoro-3-buten-2-one (26.43 g, 157.2 mmol, 1.51 equiv) was added.

The flow reactor consisted of two feed solution inlets and an outlet to a receiving vessel. The flow reactor schematic is shown in FIG. 1.

The ester solution was pumped to one flow reactor inlet. Potassium tert-amylate solution was pumped to the second reactor inlet. Trifluoroacetic anhydride was added continuously to the receiver vessel. Triethylamine was added continuously to the receiver vessel.

The flow rates were: 13 mL/min ester solution, 7.8 mL/min potassium tert-amylate solution, 3.3 mL/min trifluoroacetic anhydride and 4.35 mL/min triethylamine.

Charged toluene (50 mL) and potassium trifluoroacetate (0.64 g, 4.21 mmol, 0.04 equiv) to the receiver vessel. The flow reactor was submerged in a −10° C. bath and the pumps were turned on. The batch temperature in the receiver vessel was maintained at 5 to 10° C. throughout the run using a dry ice/acetone bath. After 13.5 min the ester solution was consumed, the reactor was flushed with toluene (10 mL) and the pumps were turned off.

The resulting yellow slurry was warmed to room temperature and aged for 4.5 h. Charged methanol (160 mL) to afford a homogeneous solution which contained 81.20 LCAP diene.

The solution of diene (573 mL) was used without purification in the subsequent reaction.

Cyclization

3-Chloro-5-((2-oxo-4-(trifluoromethyl)-1,2-dihydropyridin-3-yl)oxy)benzonitrile (E)

To a solution of diene in PhMe/MeOH (573 mL; 40.69 g, 104.4 mmol theoretical) was charged methanol (25 mL). Ammonia (32 g, 1.88 mol, 18 equiv based on theoretical) was added and the solution was warmed to 60° C. The reaction was aged at 60° C. for 18 h. The temperature was adjusted to 35-45° C. and the pressure was decreased to maintain a productive distillation rate. The batch volume was reduced to ~300 mL and methanol (325 mL) was charged in portions to maintain a batch volume between 250 and 350 mL. The heating was stopped and the system vented. The resulting slurry was cooled to room temperature and aged overnight.

The batch was filtered and the cake washed with methanol (3×, 45 mL). The wet cake was dried on the frit with suction under a nitrogen stream to afford 18.54 g of a white solid: $^1$H NMR (DMSO-$d_6$, 500 MHz): δ 12.7 (br s, 1H), 7.73 (t, 1H, J=1.5 Hz), 7.61-7.59 (m, 2H), 7.53 (t, 1H, J=2.0 Hz), 6.48 (d, 1H, J=7.0 Hz) ppm.

Step 3—Chlorination, Alkylation and Isolation of 3-Chloro-5-({1-[(4-methyl-5-oxo-4,5-dihydro-1H-1,2,4-triazol-3-yl)methyl]-2-oxo-4-(trifluoromethyl)-1,2-dihydropyridin-3-yl}oxy)benzonitrile

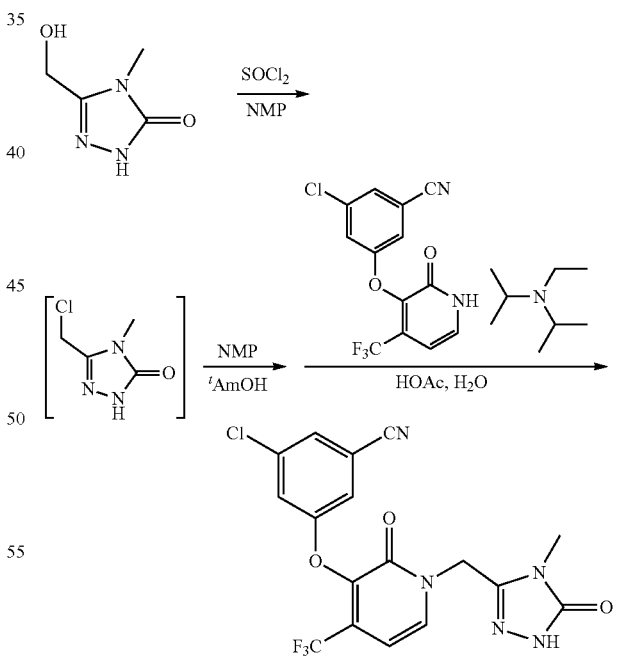

3-(Chloromethyl)-4-methyl-1H-1,2,4-triazol-5(4H)-one 3-(Hydroxymethyl)-4-methyl-1H-1,2,4-triazol-5(4H)-one (1.638 kg of 68 wt %, 8.625 mol) and N-methylpyrrolidinone (8.9 L) was charged into a 30 L vessel. The suspension was aged for 10 h at ambient temperature. The slurry was filtered through a 4 L sintered glass funnel under N₂ and the filter cake (mainly NaCl) was washed with NMP (2.23 L). The combined filtrate and wash had a water content of 5750 mg/mL. The solution was charged to a 75 L flask equipped with a 2N NaOH scrubber to capture off-gasing vapors. Thionyl chloride (0.795 L, 10.89 mol) was added over 1 h and the temperature rose to 35° C. HPLC analysis indicated that the reaction required an additional thionyl chloride charge (0.064 L, 0.878 mol) to bring to full conversion. The solution was warmed to 50° C., placed under vacuum at 60 Torr (vented to a 2N NaOH scrubber), and gently sparged with subsurface nitrogen (4 L/min). The degassing continued for 10 h until the sulfur dioxide content in the solution was <5 mg/mL as determined by quantitative GC/MS. The tan solution of 3-(chloromethyl)-4-methyl-1H-1,2,4-triazol-5(4H)-one in NMP weighed 13.0 kg and was assayed at 9.63 wt % providing 1.256 kg (97% yield).

3-chloro-5-((1-((4-methyl-5-oxo-4,5-dihydro-1H-1,2,4-triazol-3-yl)methyl)-2-oxo-4-(trifluoromethyl)-1,2-dihydropyridin-3-yl)oxy)benzonitrile To a 75 L flask was charged a 9.63 wt % solution of 3-(chloromethyl)-4-methyl-1H-1,2,4-triazol-5(4H)-one in NMP (11.6 kg, 7.55 mol), 3-chloro-5-((2-oxo-4-(trifluoromethyl)-1,2-dihydropyridin-3-yl)oxy)benzonitrile (2.00 kg, 6.29 mol), NMP (3.8 L) and 2-methyl-2-butanol (6.0 L). To the resulting suspension was slowly added N,N-diisopropylethylamine (4.38 L, 25.2 mol) over 4 h. The reaction was aged 18 h at ambient temperature. The reaction is considered complete when HPLC indicated <1% 3-chloro-5-((2-oxo-4-(trifluoromethyl)-1,2-dihydropyridin-3-yl)oxy)benzonitrile remaining. The tan solution was quenched with acetic acid (1.26 L, 22.0 mol) and aged at ambient temperature overnight. The tan solution was warmed to 70° C. Water (2.52 L) was added and the batch was seeded with anhydrate Form II (134 g)(procedures for making anhydrate Form II are described in WO2014/052171). The thin suspension was aged 1 h at 70° C. Additional water (14.3 L) was added evenly over 7 h. The slurry was aged 2 h at 70° C. and then slowly cooled to 20° C. over 5 h. The slurry was filtered and washed with 2:1 NMP/water (6 L), followed by water washes (6 L×2). The filter cake was dried under N₂ to give 2.53 kg (85% yield) of a white solid that was confirmed to be crystalline Form II of the title compound by X-ray powder defraction analysis.

Example 3

Ethyl 2-(3-chloro-5-cyanophenoxy)acetate (A)

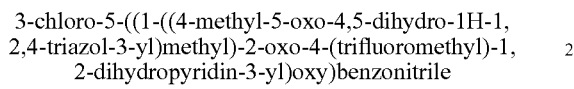

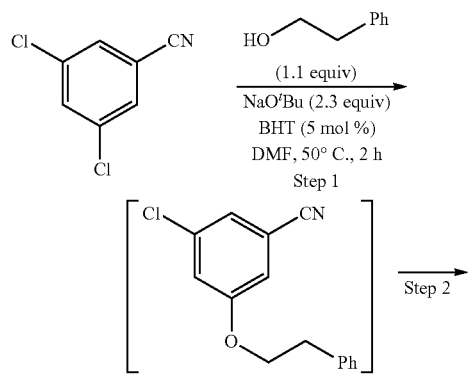

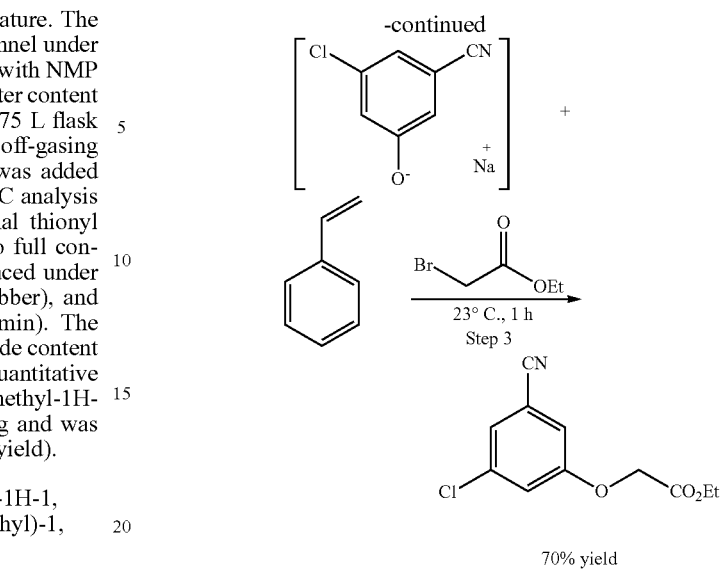

70% yield

Three step one pot sequence

Steps 1 and 2

To an oven dried 250 mL round bottom flask was added sodium 2-methylpropan-2-olate (12.85 g, 134 mmol) and BHT (0.641 g, 2.91 mmol) then added DMF (30 mL). After 10 min, a light yellow solution resulted. 2-Phenylethanol (7.66 ml, 63.9 mmol) was added and the solution exothermed to 35° C. The light yellow solution was warmed to 55° C. and then a solution of 3,5-dichlorobenzonitrile (10 g, 58.1 mmol) in DMF (15 mL) was added over 2 h via syringe pump. The resulting red-orange suspension was aged at 55-60° C. After 2 h, HPLC showed >98% conversion to the sodium phenolate.

Step 3

The suspension was cooled to 10° C., then ethyl 2-bromoacetate (8.70 ml, 78 mmol) was added over 1 h while maintaining the temperature <20° C. The resulting mixture was aged at ambient temperature. After 1 h, HPLC showed >99% conversion to the title compound.

Work-Up and Isolation:

To the suspension was added MTBE (50 mL) and H₂O (50 mL) and the layers were separated. The organic layer was washed with 20% aq brine (25 mL). The organic layer was assayed at 12.5 g (90% yield). The organic layer was concentrated to ~38 mL, diluted with hexanes (12.5 mL) and then cooled to 5° C. The solution was seeded with 0.28 g (2 wt %) of crystalline ethyl 2-(3-chloro-5-cyanophenoxy)acetate and aged 0.5 h at 5° C. to give a free flowing slurry. Hexane (175 mL) was added to the slurry over 1 h at 0-5° C. The slurry was filtered at 0-5° C., washed with hexane (50 mL) and dried under a nitrogen sweep to give 9.8 g (70% yield) of the title compound as a white crystalline solid. Seed was used to advance the crystallization, but the crystalline product can be precipitated and isolated without seed by allowing the solution to age at 0-5° C. for at least about 2 hours.

What is claimed is:

1. A method for synthesizing a compound of Formula F

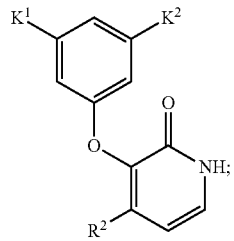

wherein $K^1$ and $K^2$ are independently $CH_3$, $CF_3$, $CHF_2$, $CH_2CF_3$, $OCH_3$, Cl, Br, F, CN or $SCH_3$, and $R^2$ is $CF_3$, Cl or Br, comprising Step 1—conducting an aldol addition of an ester of Formula B

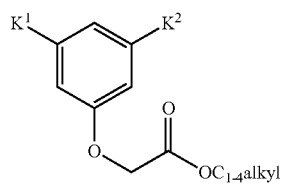

with a compound for Formula C

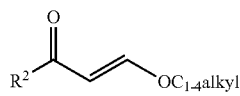

in the presence of a first base in a hydrocarbon or ethereal organic solvent at a first reduced temperature, wherein the first base is a metal alkoxide or metal amide base, to form Intermediate D, and optionally isolating Intermediate D

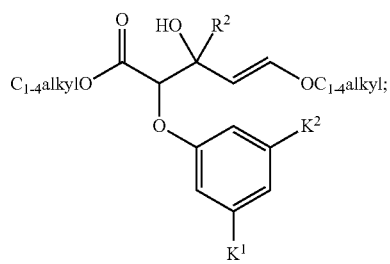

Step 2—reacting Intermediate D with an organic acid anhydride or sulfonyl chloride in the presence of a second base, wherein the second base is a tertiary amine base, at a second reduced temperature in a hydrocarbon or ethereal organic solvent, which solvent can be the same or different as that in Step 1, to form Intermediate E, and optionally isolating Intermediate E

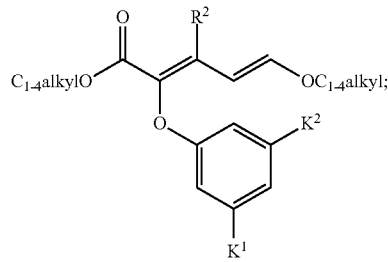

and

Step 3—cyclizing Intermediate E in the presence of a nitrogen source having formula $NH_{3+n}X_n$, wherein $X_n$=a non-coordinating counteranion and n=0 or 1, at a first elevated temperature in a mixture of alcohol and organic solvent to make the compound of Formula F.

2. A method for synthesizing a compound of Formula I

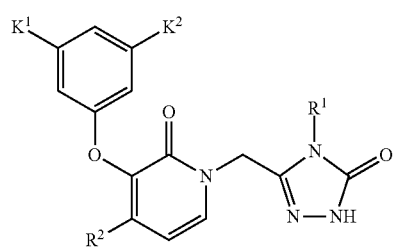

wherein $R^1$ is $C_{1-6}$ alkyl, $K^1$ and $K^2$ are independently $CH_3$, $CF_3$, $CHF_2$, $CH_2CF_3$, $OCH_3$, Cl, Br, F, CN or $SCH_3$, and $R^2$ is $CF_3$, Cl or Br, comprising Step 4—coupling the compound of Formula F

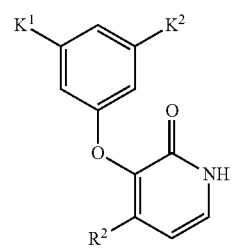

wherein the compound of Formula F is made by the process as defined in claim 1, with a compound of Formula A

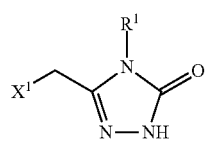

wherein $X^1$ is a leaving group, in the presence of a third base selected from an inorganic base or a tertiary amine base in a polar aprotic or protic solvent to yield the compound of Formula I.

3. The method for synthesizing the compound of Formula I according to claim 2 wherein the first base is selected from: potassium tert-amylate, sodium bis(trimethylsilyl)amide, potassium tert-butoxide, sodium tert-butoxide, lithium diisopropylamide, sodium ethoxide or potassium ethoxide.

4. The method for synthesizing the compound of Formula I according to claim 2 wherein the first reduced temperature is in a range of about 15° C. to about −50° C.

5. The method for synthesizing the compound of Formula I according to claim 2 wherein the hydrocarbon or ethereal organic solvent is selected from: toluene, tetrahydrofuran, diethyl ether, methyl tert-butyl ether, 2-methyltetrahydrofuran or xylene.

6. The method for synthesizing the compound of Formula I according to claim 2 wherein the organic acid anhydride or sulfonyl chloride is selected from: trifluoroacetic anhydride, methanesulfonyl chloride, acetic anhydride, trifluoromethanesulfonyl chloride, or p-toluenesulfonyl chloride.

7. The method for synthesizing the compound of Formula I according to claim 2 wherein the second base is selected from: trimethylamine, dimethylethylamine, triethylamine, 1,4-diazobicyclo-[2,2,2]-octane, diisopropylethylamine or dicyclohexylethylamine.

8. The method for synthesizing the compound of Formula I according to claim 1 wherein the second reduced temperature is in a range of about 15° C. to about −50° C.

9. The method for synthesizing the compound of Formula I according to claim 2, wherein Intermediate D and Intermediate E are not isolated and Step 1 is conducted in a flow reactor comprising two feed solution inlets and an outlet to a receiving vessel, wherein:
the ester of Formula B and the compound of Formula C in the hydrocarbon or ethereal organic solvent are pumped to one flow reactor inlet;
the first base in the hydrocarbon or ethereal organic solvent is pumped to the second flow reactor inlet;
the organic acid anhydride or sulfonyl chloride is added continuously to the receiver vessel;
and the second base is added continuously to the receiver vessel.

10. The method for synthesizing the compound of Formula I according to claim 2 wherein the nitrogen source is $NH_3$.

11. The method for synthesizing the compound of Formula I according to claim 2 wherein the first elevated temperature is in a range of about 25° C. to about 80° C.

12. The method for synthesizing the compound of Formula I according to claim 2 wherein the mixture of alcohol and organic solvent, wherein the alcohol is selected from methanol, ethanol, n-propanol, isopropanol, tert-butanol, or tert-amyl alcohol, and the organic solvent is selected from tetrahydrofuran, diethyl ether, methyl tert-butyl ether, 2-methyltetrahydrofuran, toluene or xylene.

13. The method for synthesizing the compound of Formula I according to claim 2 wherein $X^1$ is: halogen, OMs, OTs, OBs, $OP(O)(OR^i)_2$, $OC(O)R^i$, $OC(O)OR^i$ or $OC(O)NR^iR^{ii}$, wherein $R^i$ and $R^{ii}$ are independently selected from H or $C_{1-6}$alkyl.

14. The method for synthesizing the compound of Formula I according to claim 2 wherein the third base is selected from: sodium hydroxide, lithium hydroxide, potassium hydroxide, sodium carbonate, lithium carbonate, potassium carbonate, cesium hydroxide, cesium carbonate, sodium hydrogen carbonate, potassium hydrogen carbonate, lithium hydrogen carbonate, lithium fluoride, sodium fluoride, potassium fluoride, cesium fluoride, lithium tert-butoxide, sodium tert-butoxide, potassium tert-butoxide, sodium phosphate, potassium phosphate, trimethylamine, dimethylethylamine, triethylamine, 1,4-diazobicyclo-[2,2,2]-octane, diisopropylethylamine, or dicyclohexylethylamine.

15. The method for synthesizing the compound of Formula I according to claim 2 wherein the polar aprotic or protic solvent is a mixture of alcohol and organic amide.

16. The method for synthesizing the compound of Formula I according to claim 2 wherein Step 4 is conducted at a second elevated temperature.

17. The method for synthesizing the compound of Formula I according to claim 16 wherein the second elevated temperature is in a range of about 25° C. to about 80° C.

18. The method for synthesizing the compound of Formula I according to claim 17 wherein the second elevated temperature is about 25° C.

19. The method for synthesizing the compound of Formula I according to claim 2 wherein:
the first base is selected from: potassium tert-amylate or sodium bis(trimethylsilyl)amide;
the first reduced temperature is in a range of about 0° C. to about −50° C.;
the hydrocarbon or ethereal organic solvent is toluene;
the organic acid anhydride or sulfonyl chloride is selected: trifluoroacetic anhydride or methanesulfonyl chloride;
the second base is triethylamine;
the second reduced temperature is in a range of about 0° C. to about 10° C.;
the nitrogen source is $NH_3$;
the first elevated temperature is in a range of about 60° C. to about 80° C.;
the mixture of alcohol and organic solvent is a mixture of methanol and toluene;
$X^1$ is chloro;
the third base is N,N-diisopropylethylamine; and
the polar aprotic or protic solvent is a mixture of tert-amyl alcohol and 1-methyl-2-pyrrolidinone.

20. The method for synthesizing the compound of or Formula I according to claim 2, further comprising making the ester of Formula B

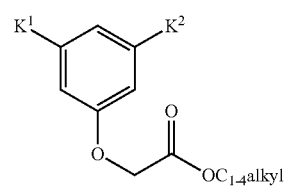

by reacting a compound of Formula G

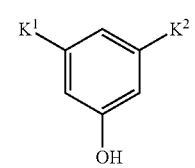

with a compound of Formula H

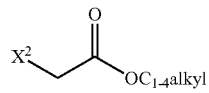

wherein $X^2$ is a halide or pseudo halide, is in the presence of a fourth base in an organic polar aprotic solvent at a third elevated temperature, wherein the fourth base is a tertiary amine or inorganic carbonate, to make the ester of Formula B.

21. The method according to claim 20, wherein $X^2$ is bromo;
the fourth base is N,N-diisopropylethylamine;
the organic polar aprotic solvent N,N-dimethylformamide or acetone; and
the third elevated temperature is about 50° C.

22. The method for synthesizing the compound of Formula I according to claim 2 wherein in the compound of Formula I, $K^1$ is Cl, $K^2$ is CN, $R^1$ is $CH_3$ and $R^2$ is $CF_3$.

23. The method for synthesizing the compound Formula F according to claim 1 wherein in the compound of Formula F, $K^1$ is Cl, $K^2$ is CN and $R^2$ is $CF_3$.

* * * * *